(12) United States Patent
Cruijff

(10) Patent No.: US 11,788,938 B2
(45) Date of Patent: Oct. 17, 2023

(54) LANCE FOR A GAS ANALYSIS SYSTEM

(71) Applicant: TATA STEEL NEDERLAND TECHNOLOGY B.V., Velsen-Noord (NL)

(72) Inventor: Marcel Cruijff, Den Ilp (NL)

(73) Assignee: TATA STEEL NEDERLAND TECHNOLOGY B.V., Velsen-Noord (NL)

( * ) Notice: Subject to any disclaimer, the term of this patent is extended or adjusted under 35 U.S.C. 154(b) by 601 days.

(21) Appl. No.: 16/485,019

(22) PCT Filed: Feb. 23, 2018

(86) PCT No.: PCT/EP2018/054589
§ 371 (c)(1),
(2) Date: Aug. 9, 2019

(87) PCT Pub. No.: WO2018/166776
PCT Pub. Date: Sep. 20, 2018

(65) Prior Publication Data
US 2020/0080918 A1    Mar. 12, 2020

(30) Foreign Application Priority Data
Mar. 17, 2017  (EP) .................................. 17161615

(51) Int. Cl.
*G01N 1/24* (2006.01)
*G01N 33/00* (2006.01)
*G01N 1/22* (2006.01)

(52) U.S. Cl.
CPC ........... *G01N 1/24* (2013.01); *G01N 33/0029* (2013.01); *G01N 2001/2282* (2013.01)

(58) Field of Classification Search
CPC ................. G01N 1/24; G01N 33/0029; G01N 2001/2282; G01N 1/2247
USPC ........................... 73/863.44, 863.53, 863.54
See application file for complete search history.

(56) References Cited

U.S. PATENT DOCUMENTS 4,054,060 A * 10/1977 Ueno .................... G01N 1/2258
73/864.31
4,874,407 A   10/1989 Lefkowitz
2010/0071485 A1   3/2010 Koteskey

FOREIGN PATENT DOCUMENTS

| CN | 103344462 A | 10/2013 |
| DE | 3234322 A1 | 3/1984 |
| EP | 2794931 A1 | 10/2014 |
| JP | S6088253 U | 6/1985 |

(Continued)

OTHER PUBLICATIONS

Notification of Reason for Rejection dated Dec. 17, 2021 to Tata Steel Nederland Technology BV for Japanese Patent Application No. 2019-550618.

(Continued)

*Primary Examiner* — Daniel S Larkin
*Assistant Examiner* — Nashmiya S Fayyaz
(74) *Attorney, Agent, or Firm* — Vorys, Sater, Seymour and Pease LLP

(57) ABSTRACT

A gas sampling lance with a gas sample pipe for sampling gases wherein the gas sample pipe is divided in a lance pipe and a connecting pipe which connects the lance pipe to a gas scrubber, a first scraper to clean the inside of the lance pipe and a second scraper to clean the inside of the connecting pipe.

18 Claims, 5 Drawing Sheets

(56) References Cited

FOREIGN PATENT DOCUMENTS

| | | | |
|---|---|---|---|
| JP | H0321472 | * | 5/1991 |
| JP | H0658348 U | * | 8/1994 |
| JP | H0658348 U | | 8/1994 |
| JP | 2001116667 A | * | 4/2001 |
| JP | 2001116667 A | | 4/2001 |
| JP | 2002275612 A | * | 9/2002 |
| JP | 2005189149 A | | 7/2005 |
| JP | 5194493 B2 | * | 5/2013 |
| WO | 2004037389 A1 | | 5/2004 |
| WO | 2013091847 A1 | | 6/2013 |

OTHER PUBLICATIONS

International Search Report and Written Opinion dated May 22, 2018 for PCT/EP2018/054589 to Tata Steel Nederland Technology B.V. filed Feb. 23, 2018.

* cited by examiner

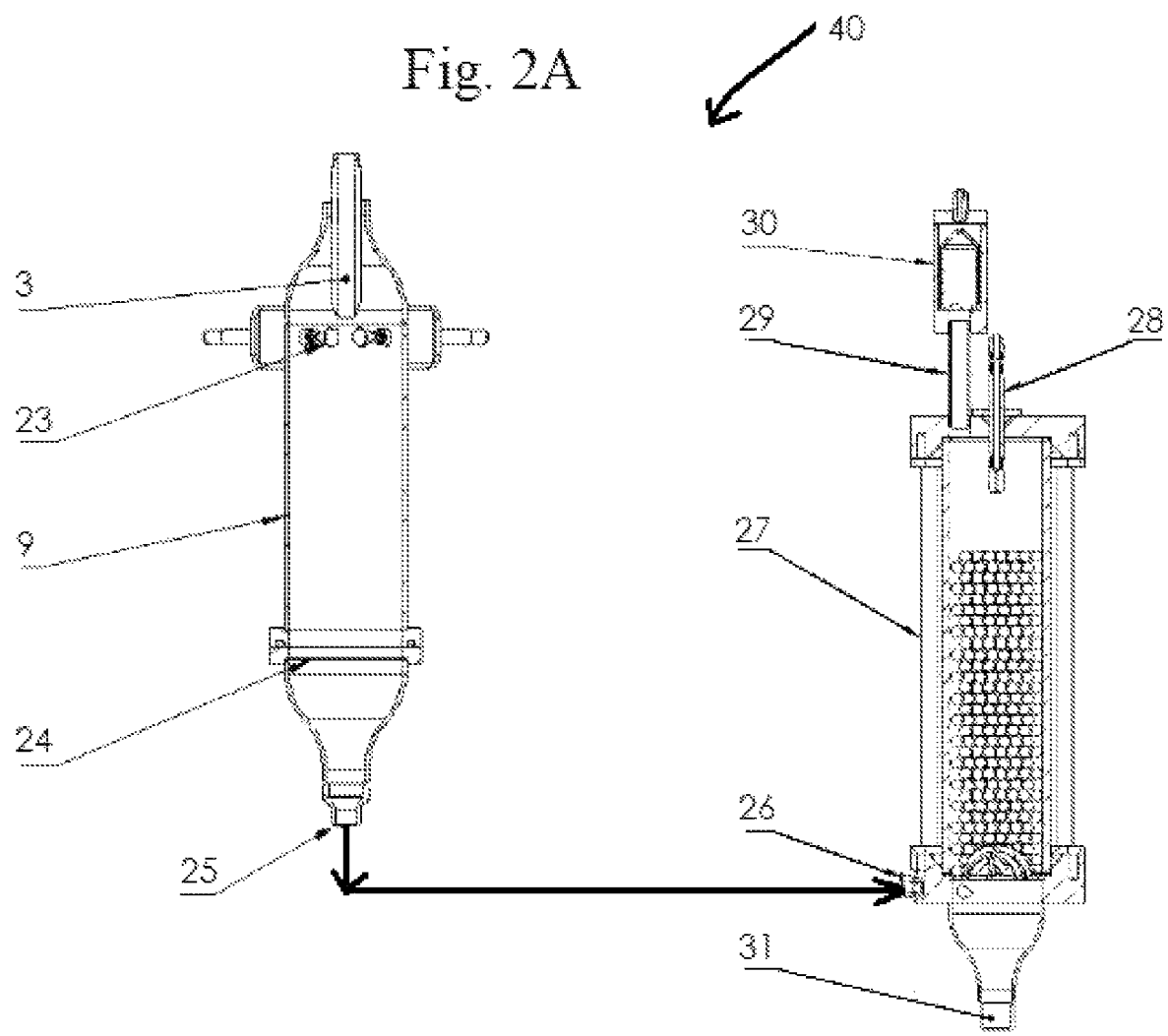

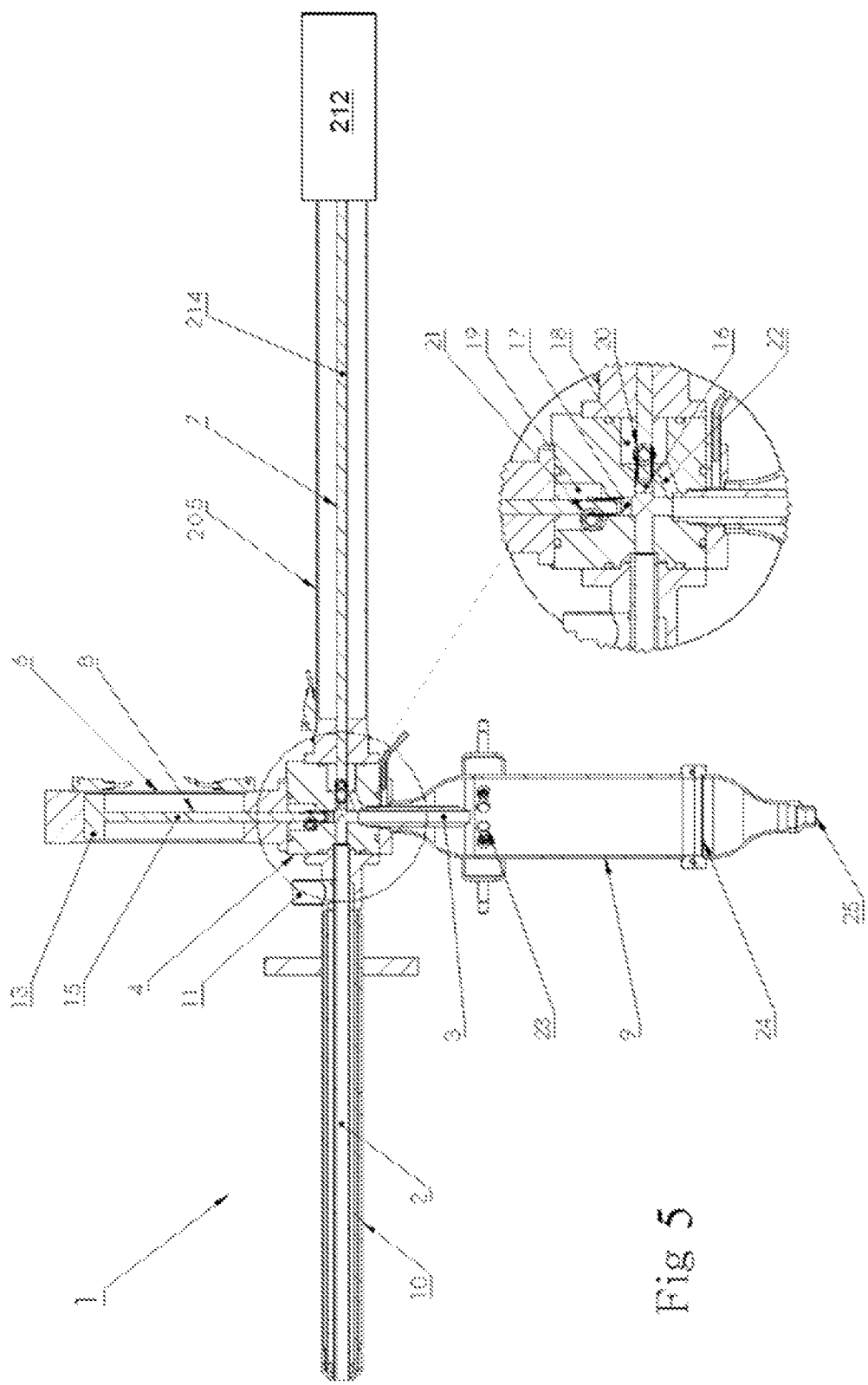

LANCE FOR A GAS ANALYSIS SYSTEM

CROSS-REFERENCE TO RELATED APPLICATIONS

This is a § 371 National Stage Application of International Application No. PCT/EP2018/054589 filed on Feb. 23, 2018, claiming the priority of European Patent Application No. 17161615.4 filed on Mar. 17, 2017.

FIELD OF THE INVENTION

The invention relates to a lance for a gas analysis system and to a gas scrubber device provided with such lance.

BACKGROUND OF THE INVENTION

In many industrial processes it is of vital importance to know the composition of gases in the process and any changes that might occur in the composition of the gases. Often these gases have to be sampled from a hot, corrosive and dust laden environment which not only requires that the gas sampling lance can withstand the hot and corrosive environment but also that the lance is frequently cleaned before the lance gets clogged with the dust carried along with the gases.

In the production of iron and steel various gases such as $CO$, $CO_2$, $O_2$, $H_2$ and $H_2O$ arise from the process together with a great amount of dust including slag and iron oxides. The temperatures in these gases could range from several hundred degrees up to 2000° C. The occurrence of these gases and the amount in which these gases are present gives important information for the control of the process.

The gas analysis systems and gas lances used for these measurements are provided with a lance pipe that protrudes into the space from which the gas has to be sampled such as a metallurgical vessel and/or the off-gas duct of such a vessel. The metallurgical vessel could be a blast furnace vessel, a smelting vessel such as the HIsarna smelting vessel (disclosed in EP2794931) or a converter vessel. Because of the high temperature and often aggressive environment lance pipes are usually made of corrosion-resistant metal alloys which can withstand high temperatures. Such lance pipes may further be provided with a cooling system to keep the temperature of the lance pipe below a certain maximum temperature.

The entrainment of dust and other particles with the gas into the lance pipe requires frequent cleaning of the lance pipe or replacement of the lance pipe. This will mean that either the sampling of process gases has to be interrupted frequently or that a double system has to be provided. A double gas sampling system or at least a system with two gas sample lances with the necessary means to change-over from the first gas sample lance to the second gas sample lance brings further cost. Besides the further costs for the gas sample lances also extra space and passages through the wall of the vessel or the off-gas duct is required which further raises the costs for such a double gas sampling system.

OBJECTIVES OF THE INVENTION

It is an objective of the present invention to provide a gas sampling lance with means to remove dust and other particles entrained with the gas from the inside of the lance pipe.

It is another objective of the present invention to provide means to remove dust and other particles entrained with the gas from the inside of a connecting pipe connected to the lance pipe.

It is another objective of the present invention to provide a gas sampling device which allows to take continuously or semi-continuously gas samples.

It is another objective of the present invention to provide a gas sampling lance wherein the means to remove dust and other particles entrained with the gas can easily be replaced.

It is still another objective of the present invention to provide a gas sampling lance that can be manufactured easily and against low costs.

DESCRIPTION OF THE INVENTION

The invention relates to a gas sampling lance and a gas scrubber. The gas scrubber having a mist chamber and a gas cleaning chamber. The connecting pipe of the lance connects to the mist chamber and the gas cooling chamber to the gas cleaning chamber.

One or more of the objectives of the invention are realized by providing a gas sampling lance with a gas sample pipe system for sampling gases wherein the gas sample pipe system is divided in a lance pipe and a connecting pipe which connects the lance pipe to the gas scrubber, a first scraper to clean the inside of the lance pipe and a second scraper to clean the inside of the connecting pipe.

The lance pipe of the gas sample pipe system of the gas sampling lance is the part of the gas sampling lance that is introduced partly into the metallurgical vessel or duct connected to the metallurgical vessel and which is made of an alloy capable of withstanding high temperatures. The gas sampling lance is used for a gas analyser device and the gas sampled should be cleaned and cooled to a sufficient low temperature to be able to transport the gases through synthetic tubes to the gas analyzers.

More often than not the gas sampled is carrying a considerable amount of dust and also larger particles that will enter the gas sample pipe and adheres for at least a part to the inside wall of the gas sample pipe. In order to prevent that the gas sample pipe gets clogged it should be cleaned or replaced from time to time. In order to be able to clean the whole length of gas sample pipe the gas sample pipe should be accessible over the complete length of the pipe. The gas sample pipe is connected to a gas scrubber which may comprise a mist chamber to catch the dust by means of the large surface area of the mist and a gas cleaning chamber, wherein the polluted water mist is separated from the sampling gas. To be able to clean the gas sample pipe with a scraper the lance pipe should be made accessible for such a scraper. According a first aspect the gas sampling pipe is provided with a lance pipe and a connecting pipe which pipes are configured at an angle to each other which makes the lance pipe and the connecting pipe separately accessible by a scraper. In this way the whole pipe trajectory from the end of the lance pipe that protrudes into the vessel or duct of the vessel to the connection of the connecting pipe with the gas scrubber can be cleaned from dust adhered to the inside of these pipes.

It is further provided that the first and/or second scraper comprises a cylinder with a piston, a piston rod and a scraper element attached to the piston rod and wherein the respective scrapers are mounted in line with respectively the lance pipe and the connecting pipe. Such a scraper can easily be controlled and allows to operate the scraper with a suitable velocity through the lance pipe and the connecting pipe.

Typically the first and second scraper are operated pneumatically but hydraulic operation of the cylinders is also possible.

Instead of pneumatic or hydraulic operation of the scrapers these can also be operated electrically. According to a further aspect it is provided that the first and/or second scraper each comprises an electric motor driving a spindle guided in a housing and/or a linear motor driving a rod guided in a housing with a scraper element attached to the spindle or the rod and wherein the respective scrapers are mounted in line with respectively the lance pipe and the connecting pipe. The housing in which the spindle or rod are guided are provided with a tight seal for both liquids and gases at the side of the lance pipe or connecting pipe.

It is further provided that the force with which a scraper is operated can be varied. More in particular it is provided that the force with which the scraper is moved through the lance pipe or the connecting pipe is different for the cleaning stroke and the retracting stroke. Because of the length of a scraper there is a risk of buckling or kinking of the scraper rod or spindle when a too large force is exerted. This could happen when the scraper element gets stuck in the lance pipe or the connecting pipe because of the amount of adhered dust and larger particles. For that reason it is typically provided that the force of the cleaning stroke is smaller than that of the return stroke, by which it is prevented that the scraper rod or spindle buckles or kinks when it gets stuck but that there is sufficient force to retract the scraper rod or spindle to its starting position.

Also different speeds can be used for the lance pipe and the connecting pipe where the amount of dust adhered to the inside of the pipe can be a determining factor for the speed of travel of a scraper element. The amount of dust adhering to the inside of the pipe per unit of time can also be taken as a determining factor for the frequency with which the cleaning operation is carried out. This could imply that the lance pipe is cleaned more frequently than the connecting pipe.

According to a further aspect the velocity with which the scraper moves through the lance pipe or the connecting pipe is monitored. A decrease in speed is an indication that the amount of adhered dust and larger particles per unit of time has increased. As a counter measure the frequency with which the lance pipe or the connecting pipe is cleaned is changed in order to get the velocity of the scraper back within a predefined range. With an increase of velocity the frequency could be lowered.

The lance pipe and connecting pipe can be positioned with respect to each other such that the pipe are directly adjacent to each other and connected by a short passageway only to allow that there is no overlap of the respective pipes. Such a configuration allows that the scraper elements and piston rods can be operated without any risk that a moving scraper would come into the path of travel of the other scraper. However, even the shortest possible passageway between lance pipe and connecting pipe gives the possibility that dust will clog in such passageway which will at least partly block the through flow of sampled gas.

With a configuration wherein the lance pipe and the connecting pipe are positioned such that the heart lines of the lance pipe and the connecting pipe intersect, both the lance pipe and the connecting pipe, that is the whole length of the gas sample pipe can be cleaned with the respective scrapers.

In order to have a free path of travel for a scraper element and to cover the whole length of the respective pipe it is provided that the length of stroke of a scraper extends from a start point at one side of where the lance pipe and the connecting pipe connect to an end point at or near the end of the lance pipe or the connecting pipe at the opposite side of where the lance pipe and the connecting pipe connect.

According to a further aspect it is provided that the scraper elements are ceramic or bronze scrapers elements. Other materials that are suitable to be used for the scraper elements are tungsten, nickel alloys and other copper alloys.

These scraper elements are mounted as scraper tips on the outer ends of the piston rods. The outer ends of the piston rods are adapted to receive such scraper tips. The scraper elements are shaped to the inside of the lance pipe or connecting pipe which will in most cases mean a cylindrical element with a circular cross-section. Depending on the temperature of the sampled gases and/or the temperature of the respective pipes a specific material will be chosen. Since the outer end of the scraper element for the lance pipe may be in direct contact with hot gases inside the metallurgical vessel or duct connected to such vessel a reliable choice for such a scraper would be an element of a ceramic material.

The scraper element for the connecting pipe is also made of a ceramic material if the temperature of the sample gas in the connecting pipe so requires. If the temperature is low enough to be able to use other materials for the scraper a suitable material would be bronze.

The diameter of the scraper elements will typically be taken smaller than the inner diameter of the lance pipe and connecting pipe to account for any temperature related expanding of the pipes and/or scraper elements. This might mean that some dust residue could remain in the pipes after the scraper element has moved through the pipe but that is of minor importance since the aim is only to keep the pipes open at all times.

Since the piston rods and scraper elements are moved periodically through a relatively high temperature environment the temperature of the piston rods and scraper elements will also increase during operation. This could be an issue for especially the piston rod since the piston rod will move at least partly in and out of the cylinder passing therewith a cylinder seal. Since the cylinder seal will be in most cases a flexible material which will not withstand elevated temperatures for a long time the temperature of the piston rod should be controlled such that the temperature will remain below a certain predefined maximum temperature. For that reason at least one inlet for a cooling medium is provided wherein the cooling medium is used for the cooling of the piston rod and/or scraper element of at least one scraper.

According to another aspect it is provided that the lance pipe, the connecting pipe, the cylinder or housing of the first scraper and the cylinder or housing of the second scraper are connected by means of a connecting member. This connecting member or connecting block allows to use separate parts for the gas sample lance an also allows an easy assembly and replacement of parts.

The use of a connecting member further allows to provide the at least one inlet for the cooling medium in the connecting member. Such an inlet is further provided with a suitable connection to connect the inlet with a supply of cooling medium, for instance a pressurised supply of cooling medium.

A suitable embodiment provides that the at least one inlet for the cooling medium connects to a recess provided in the connecting member and wherein the recess encloses at least part of one piston rod between the location where the lance pipe and the connecting pipe connect and the cylinder associated with that piston rod. A recess that encloses part of the piston rod outside the cylinder allows to bring the cooling medium against all sides of the part of the piston rod in the recess.

According to a further aspect the recess is provided with a drain, wherein the drain connects to the connecting pipe downstream of the location where the lance pipe and the connecting pipe connect. In order to have an effective cooling of the piston rod and/or the scraper element the cooling medium should be replaced continuously or semi-continuously. For that a certain flow rate of the cooling medium will be necessary for which a certain supply has to be provided as well as an outlet for the supplied cooling medium. The drain should not connect directly to the outside environment because that could result in outside air or gases entering the gas sampling lance resulting in unreliable gas analysis.

It turned out that a suitable way to supply the cooling medium to cool the piston rod and/or scraper element of at least one scraper is to supply the cooling medium as a mist. The advantage is that an effective cooling is obtained whereas the needed volume of cooling medium is far less than when the cooling medium is supplied as a liquid. An effective cooling medium is water supplied as a mist.

The cylinder of the first and/or second scraper is a gas driven cylinder. Typically the cylinder of the first and/or second scraper is a Nitrogen-gas or an inert gas driven cylinder. By using such a gas to drive the cylinder there is no chance that the gas analysis will be disturbed in case of a leaking cylinder.

The gas sample lance is connected to a gas scrubber provided with a mist chamber and a gas cleaning chamber, wherein the connecting pipe of the lance connects to the mist chamber and the mist chamber to the gas cleaning chamber.

BRIEF DESCRIPTION OF THE DRAWINGS

The invention will be further explained by means of the example shown in the drawing, in which:

FIG. 5 schematically shows a linear motor for driving a rod.

DETAILED DESCRIPTION OF THE DRAWINGS

Figure 1:
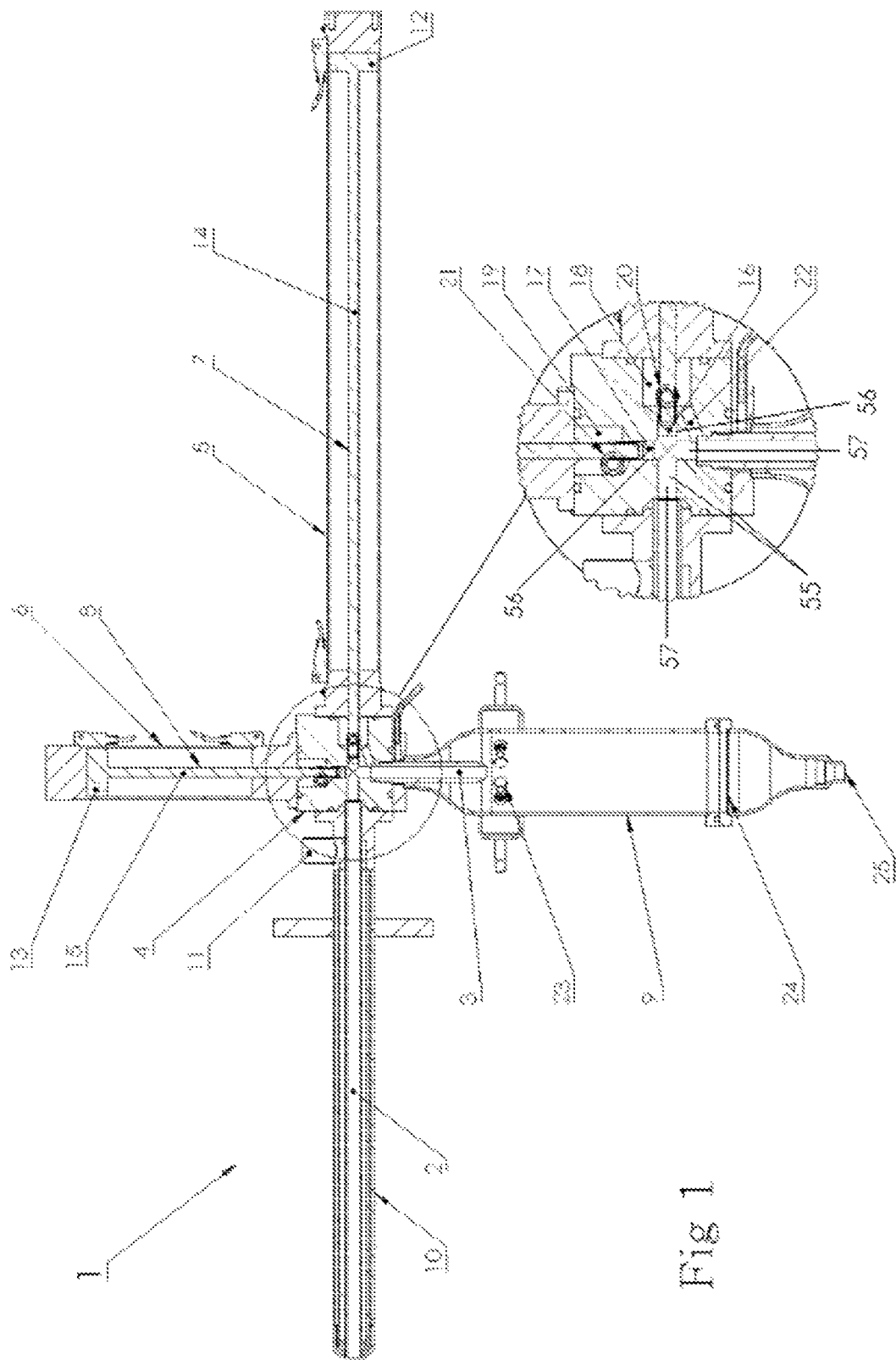
FIG. 1 shows a gas sampling lance and a mist chamber attached thereto in cross-section and an enlarged view of a connecting member.
Figure 3:
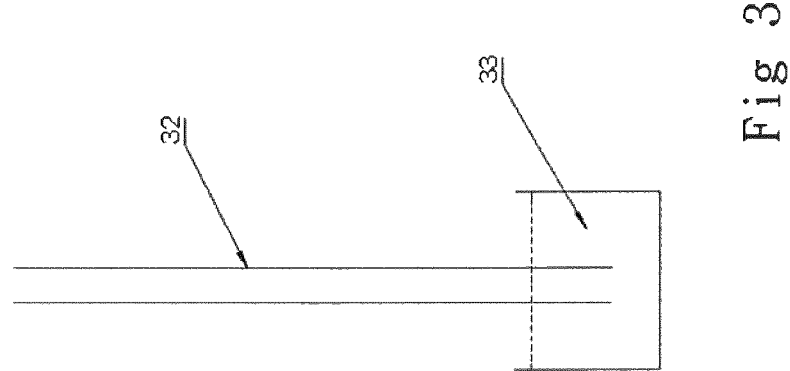
FIG. 3 shows a drain system that connects to the cleaning chamber.
Figure 2:
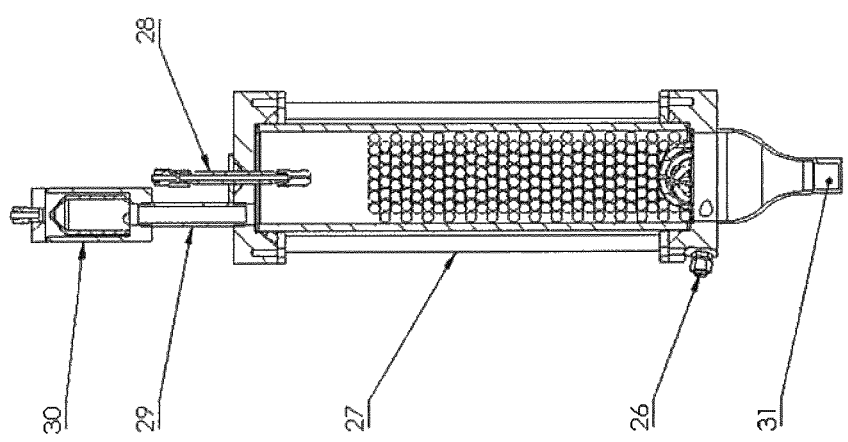
FIG. 2 shows a gas cleaning chamber.

In FIG. 1 a gas sampling lance 1 is shown provided with a lance pipe 2, a connecting pipe 3, a connecting block 4, a first and second cylinder 5,6 with respectively a first and second scraper 7,8 and a mist chamber 9. The gas sampling lance 1 is connected to a mist chamber 9 of a gas scrubber 40. The gas scrubber 40 is provided with the mist chamber 9 and a gas cleaning chamber 27. FIG. 2 shows the mist chamber 9. The mist chamber 9 connects through outlet 25 with inlet 26 of gas cleaning chamber 27 as shown in FIG. 2A.

The lance pipe 2 is provided at the outside with a cooling jacket 10 with an inlet 11 and outlet (not shown in the drawing) for a cooling medium for the lance pipe 2. The cooling jacket 10 is necessary to provide sufficient cooling of the lance pipe 2 for the part of the lance pipe that enters the vessel or duct but typically also for the downstream part outside the vessel or duct since the temperature of the sampled gas will not drop considerably inside the lance pipe 2.

The lance pipe 2 connects to the connecting member 4 in a manner that it can be easily be replaced for instance by bolting the lance pipe 2 to the connecting block 4.

The lance pipe 2 and the connecting pipe 3 connect by means of channels 55 provided in the connecting block 4 that are in line with lance pipe and connecting pipe. These channels 55 with the lance pipe 2 and connecting pipe 3 form together the gas sample pipe. The lance pipe and connecting pipe are positioned with respect to each other such that the lance pipe and connecting pipe are directly adjacent to each other and connected by a short passageway provided by portions 57 of the channels 55 to allow that there is no overlap of the respective pipes.

The channels 55 in the connecting block have portions 56 that extend beyond the spot where the lance pipe 2 and connecting pipe 3 connect through the connecting block 4 to the outside faces of the connecting block 4. These extended channels 56 form the respective points of entry for first and second scraper 7,8. The first and second cylinder 5,6 of first and second scraper 7,8 are mounted on the connecting block by means of bolts or the like such that these cylinders and/or parts of the cylinders can be replaced easily when necessary.

The first and second scraper 7,8 comprise a piston 12,13, a piston rod 14,15 connected to the respective pistons 12,13 and a scraper tip 16,17 at the end of each of the piston rods 14,15. The extended channels in connecting block 4 widen at their respective outer ends to form recesses 18,19. In the most retracted position of the scrapers 7,8 the scraper tips 16,17 are at least partially in the respective recesses 18,19.

The recesses 18,19 are each provided with an inlet 20,21 which connect to a supply of cooling medium such as atomized water. The use of a liquid medium that is sprayed as a mist provides sufficient cooling whereas the total volume of the cooling medium can be kept at a minimum. This is important because the used cooling medium is drained through the scrubber connected to the gas sampling lance 1 which is only capable of handling a certain maximum volume of liquid medium.

Recess 18 is provided with a drain channel 22 which connects the recess with the connecting pipe 3. A similar drain could be provided for the other recess 19 which, however in the shown embodiment is not necessary because of the vertical or about vertical position of scraper 8 and connecting pipe 3 and the smaller length of connecting pipe 3 compared to that of lance pipe 2. The cooling medium used in recess 19 flows in downward direction either directly along the scraper tip 17 into connecting pipe 2 or indirectly by first flowing into the lance pipe 3 and then into connecting pipe 2. The diameter of the scraper tips 16,17 are taken smaller than the diameters of the respective pipes to prevent that the scrapers 16,17 could get stuck in the pipes because of thermal expansion of the scrapers and or pipes. This gives sufficient play to drain the cooling medium from recess 19 through the connecting pipe 2.

In the mist chamber 9 the sampled gas is cooled by means of a cooling medium supplied to the cooling chamber 9. Also in the cooling chamber typically an atomized liquid is used to cool the sampled gas. The mist chamber is provided with inlets 23 to supply a mist of cooling medium into the sampled gas in the chamber. At the lower end of the mist chamber 9 a grid 24 is provided to prevent that accretions fall into outlet 25 of the mist chamber and cause blockage of the scrubber system.

The mist chamber 9 connects through outlet 25 with inlet 26 of gas cleaning chamber 27. In FIG. 2 the gas cleaning chamber is at least partially filled with glass beads and is provided with an inlet 28 for a cleaning liquid for which water can be used and an outlet 29 for cooled and cleaned sampled gas. In the outlet 29 a float 30 is provided which closes gas outlet 29 in case too much cooling and/or cleaning liquid has come into the gas cleaning chamber 27. In that way it is prevented that any liquid could come in the downstream system with the gas analysis equipment.

The water is sprayed over the glass beads and the sampled gas in between the glass beads and leaves with the collected dust from the gas cleaning chamber 27 through outlet 31, connected to drain pipe 32 and is collected in container 33. Since the gas sampling is driven by applying a pressure lower than atmospheric pressure the drain pipe 32 is taken long enough to prevent that liquid could be forced back into the gas cleaning chamber 27 by the higher atmospheric pressure.

In operation gas is drawn in the gas sample pipe because of the pressure in the system which is by means of a suction pump kept below atmospheric pressure and below the pressure in the vessel or duct from which the gas is to be sampled. With the sampled gas dust is carried along into the gas sample pipe which will adhere to the walls of the gas sample pipe. To prevent clogging the dust adhered to the walls is periodically removed by operating the scrapers. Most of the dust will adhere to the wall of the lance pipe 2. To remove the dust the scraper 7 is moved from the start position over the length of the lance pipe 2 to the end of the lance pipe therewith pushing most of the dust back into the vessel or duct. Part of the dust might remain on the wall and part of the dust might be pushed in the other direction when retracting the scraper back to its start position. That part of the dust might come in the connecting pipe and/or in the recess 18. The dust ending up in the connecting pipe 2 is in its turn removed by the second scraper 8 which moves from its start position to the end of the connecting pipe 2 and back again. Part of the dust that comes into the recesses is removed by means of the liquid mist used for the cooling of the scraper tips and piston rods and will be taken into the gas cooling chamber 9.

Figure 4:
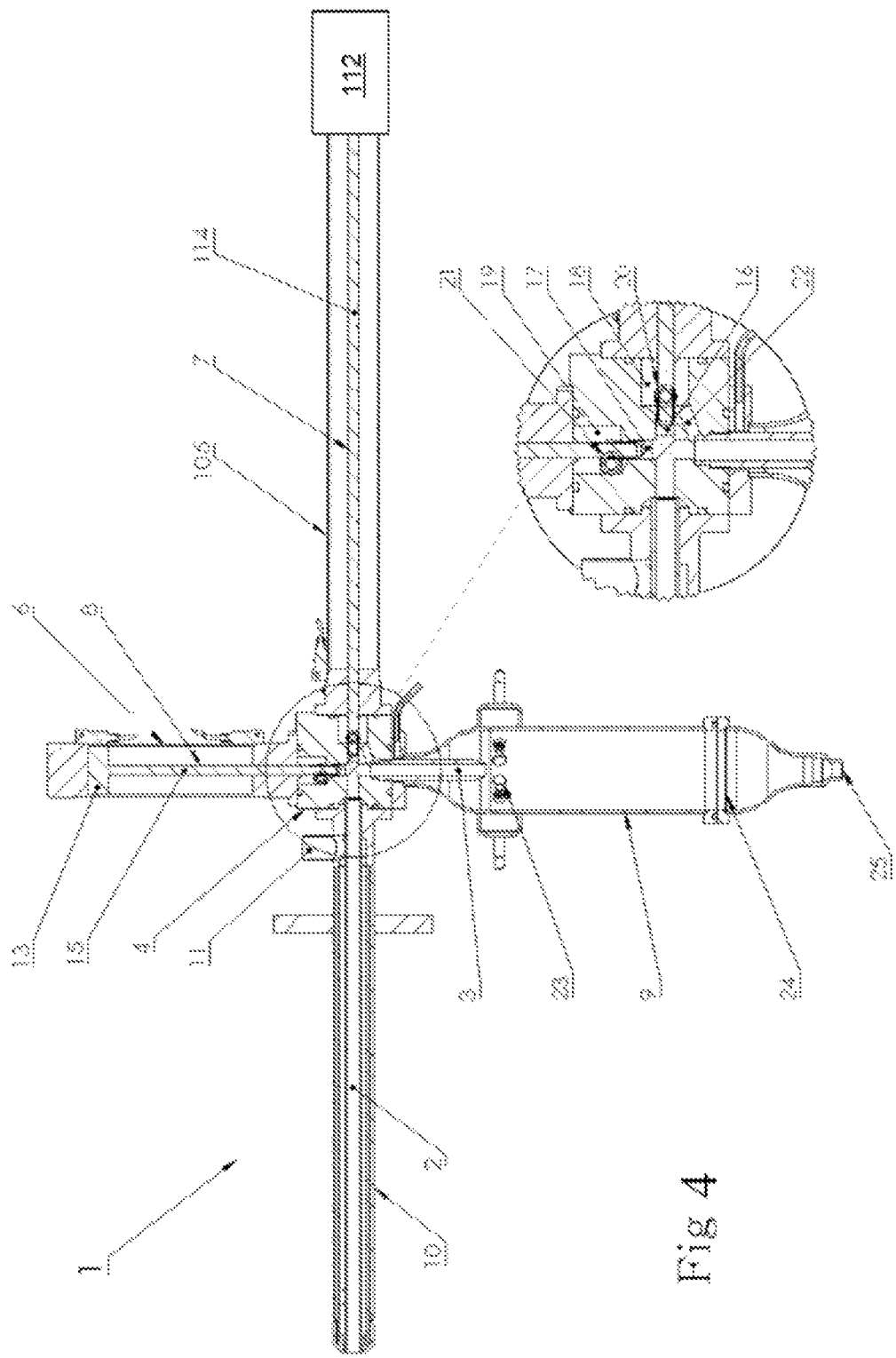
FIG. 4 schematically shows an electric motor for rotating a spindle.

FIG. 4 schematically shows an electric motor 112 for rotating a spindle 114 attached to a scraper tip 17. The electric motor 112 and spindle 114 can be conventionally moved along the longitudinally direction of the housing 105.

FIG. 5 schematically shows a linear motor 212 for driving a rod 214 attached to a scraper tip 17. The rod 214 can be conventionally moved by the linear motor 212 along the longitudinally direction of the housing 205.

The scrapers are typically used in succession with firstly the first scraper 7 and secondly the second scraper 8. The scrapers can be moved to and fro relatively rapidly with the gas driven cylinders such that the flow of sampled gas will hardly be disturbed. By moving the piston at a certain speed and at a certain time interval the temperature increase of the scraper tip and piston rod because of the hot environment and hot gas can be kept at a minimum.

During the scraping operation the otherwise open connection with the duct or vessel is temporarily blocked, but the volume of gas present in the mist chamber and the cleaning chamber provides a sufficient large gas buffer to continuously suck gas to the gas analysers.

The invention claimed is:

1. A gas sampling lance comprising
a gas sample pipe system for sampling gases, wherein the gas sample pipe system comprises a lance pipe for protruding into a space from which the gas has to be sampled and a connecting pipe for connecting the lance pipe to a gas scrubber,
a first scraper to clean the inside of the lance pipe, and
a second scraper to clean the inside of the connecting pipe,
wherein the lance pipe and the connecting pipe are configured at an angle to each other;
wherein the respective scrapers are mounted in line with respectively the lance pipe and the connecting pipe;
wherein the lance pipe, the connecting pipe, the first scraper and the second scraper are connected to a connecting block, where the connecting block has a first pair of opposed faces and a second pair of opposed faces,
wherein the lance pipe is connected to one face of the first pair of faces and the first scraper is connected to the other face of the first pair of faces at a point of entry into the connecting block for the first scraper,
wherein the connecting pipe is connected to one face of the second pair of opposed faces and the second scraper is connected to the other face of the second pair of opposed faces at a point of entry into the connecting block for the second scraper;
wherein the lance pipe and the connecting pipe connect to the connecting block such that channels provided in the connecting block are in line with the lance pipe and the connecting pipe and provide a passageway between the lance pipe and the connecting pipe for passage of sampled gas from the lance pipe to the connecting pipe, wherein these channels with the lance pipe and connecting pipe form together the gas sample pipe system;
wherein portions of the channels in the connecting block respectively extend, beyond the passageway between the lance pipe and connecting pipe, through the connecting block to the faces of the connecting block to form the respective points of entry for the first scraper and the second scraper;
wherein the connecting block has a block shape wherein the first pair of opposed faces connect to and are perpendicular to the second pair of opposed faces;
wherein the lance pipe and the connecting pipe are positioned such that center lines of the lance pipe and the connecting pipe intersect;
wherein the respective scrapers are mounted in line with respectively the lance pipe and the connecting pipe, and
wherein the portions of the channels in the connecting block have respective outer ends and widen at their respective outer ends to form respective first and second recesses where the first scraper and the second scraper are connected to the connecting block, and the first scraper is mounted in line with the first recess and the second scraper is respectively mounted in line with the second recess.

2. The lance according to claim 1, wherein the first scraper and the second scraper each comprises a respective cylinder with a respective piston within the respective cylinder, a respective piston rod extending from the respective piston to a respective piston rod end distal to the respective piston, and a respective scraper element attached to the respective piston rod end distal to the piston, and wherein each respective recess encloses at least part of the respective piston rod outside the respective cylinder.

3. The lance according to claim 1, wherein the first and/or second scraper comprises an electric motor driving a spindle guided in a housing and/or a linear motor driving a rod guided in a housing with a scraper element attached to the spindle or the rod and wherein the respective scrapers are mounted in line with respectively the lance pipe and the connecting pipe.

4. The lance according to claim 1, wherein first and second inlets for a cooling medium are provided in the connecting block,
wherein the first inlet for the cooling medium connects to the first recess provided in the connecting block,
wherein the second inlet for the cooling medium connects to the second recess provided in the connecting block.

5. The lance according to claim 1, wherein the length of stroke of the first or second scraper extends from a start point at one side of where the lance pipe and the connecting pipe connect to respectively an end point at or near the end of the lance pipe or the connecting pipe at the opposite side of where the lance pipe and the connecting pipe connect.

6. The lance according to claim 2, wherein the scraper elements are ceramic or bronze scraper elements.

7. The lance according to claim 2, wherein at least one inlet for a cooling medium is provided, wherein the cooling medium is used for the cooling of the piston rod and/or scraper element of at least one scraper.

8. The lance according to claim 7,
wherein the cylinder of the first scraper is connected to the other face of the first pair of faces at the point of entry into the connecting block for the first scraper,
wherein the cylinder of the second scraper is connected to the other face of the second pair of opposed faces at the point of entry into the connecting block for the second scraper.

9. The lance according to claim 8, wherein the at least one inlet for the cooling medium is provided in the connecting block, wherein the cooling medium is used for the cooling of the piston rod and/or scraper element of at least one scraper.

10. The lance according to claim 9, wherein the at least one inlet for the cooling medium respectively connects to at least one of the first recess or the second recess provided in the connecting block.

11. The lance according to claim 10, wherein the at least one of the first recess or the second recess having the inlet for the cooling medium is provided with a drain and wherein the drain connects to the connecting pipe downstream of the passageway.

12. The lance according to claim 7, wherein the cooling medium to cool the piston rod and/or scraper element of at least one scraper is supplied as a mist.

13. The lance according to claim 1, wherein the cylinder of the first and/or second scraper is a gas driven cylinder.

14. The lance according to claim 12, wherein the cylinder of the first and/or second scraper is a Nitrogen-gas or an inert gas driven cylinder.

15. The lance according to claim 1, wherein an outside of the lance pipe is provided with a cooling jacket with an inlet and outlet for a cooling medium for the lance pipe.

16. An apparatus comprising the gas scrubber and the lance according to claim 1, said gas scrubber comprising a mist chamber and a gas cleaning chamber, wherein the connecting pipe connects the lance to the mist chamber and a gas cooling chamber connects to the gas cleaning chamber.

17. The lance according to claim 1, wherein the first scraper comprises a first electric motor driving a first spindle guided in a first housing, and the second scraper comprises a second electric motor driving a second spindle guided in a second housing and wherein the respective first and second scrapers are mounted in line with respectively the lance pipe and the connecting pipe.

18. The lance according to claim 16, wherein the gas cleaning chamber is at least partially filled with glass beads.

* * * * *